(12) United States Patent
Negiz et al.

(10) Patent No.: US 7,154,014 B1
(45) Date of Patent: Dec. 26, 2006

(54) ALUMINA GUARD BED FOR AROMATICS TRANSALKYLATION PROCESS

(75) Inventors: Antoine Negiz, Wilmette, IL (US); Edwin P. Boldingh, Arlington Heights, IL (US); Sergio A. Pischek, Westmont, IL (US)

(73) Assignee: UOP LLC, Des Plaines, IL (US)

( * ) Notice: Subject to any disclaimer, the term of this patent is extended or adjusted under 35 U.S.C. 154(b) by 174 days.

(21) Appl. No.: 10/946,948

(22) Filed: Sep. 22, 2004

(51) Int. Cl.
*C07C 5/00* (2006.01)

(52) U.S. Cl. ........................................... 585/475
(58) Field of Classification Search ............... 585/475
See application file for complete search history.

(56) References Cited

U.S. PATENT DOCUMENTS

| | | | | |
|---|---|---|---|---|
| 3,702,886 A | 11/1972 | Argauer et al. | ............. | 423/328 |
| 3,709,979 A | 1/1973 | Chu | ............. | 423/328 |
| 3,832,449 A | 8/1974 | Rosinski et al. | ............. | 423/328 |
| 3,849,340 A | 11/1974 | Pollitzer | ............. | 252/455 Z |
| RE28,341 E | 2/1975 | Wadlinger et al. | ............. | 208/120 |
| 4,076,842 A | 2/1978 | Plank et al. | ............. | 423/328 |
| 4,159,282 A | 6/1979 | Olson et al. | ............. | 585/481 |
| 4,163,018 A | 7/1979 | Tada et al. | ............. | 260/429.9 |
| 4,241,036 A | 12/1980 | Flanigen et al. | ............. | 423/328 |
| 4,278,565 A | 7/1981 | Chen et al. | ............. | 252/455 Z |
| 4,358,362 A * | 11/1982 | Smith et al. | ............. | 208/91 |
| 4,440,871 A | 4/1984 | Lok et al. | ............. | 502/214 |
| 4,537,754 A | 8/1985 | Casci et al. | ............. | 423/277 |
| 4,556,477 A | 12/1985 | Dwyer | ............. | 208/111 |
| 4,567,029 A | 1/1986 | Wilson et al. | ............. | 423/306 |
| 4,857,666 A | 8/1989 | Barger et al. | ............. | 585/323 |
| 5,296,208 A | 3/1994 | Lesch | ............. | 423/700 |
| 5,516,736 A * | 5/1996 | Chang et al. | ............. | 502/64 |
| 5,723,710 A | 3/1998 | Gajda et al. | ............. | 585/467 |
| 5,763,720 A | 6/1998 | Buchanan et al. | ............. | 585/475 |
| 6,060,417 A | 5/2000 | Kato et al. | ............. | 502/66 |
| 6,486,372 B1 | 11/2002 | Merlen et al. | ............. | 585/467 |
| 6,613,709 B1 | 9/2003 | Merlen et al. | ............. | 502/64 |
| 6,740,788 B1 | 5/2004 | Maher et al. | ............. | 585/319 |

FOREIGN PATENT DOCUMENTS

EP  0 378 916 B1  11/1992

* cited by examiner

*Primary Examiner*—Thuan Dinh Dang
(74) *Attorney, Agent, or Firm*—John G. Tolomei; Maryann Maas

(57) ABSTRACT

A transalkylation process for reacting carbon number nine aromatics with toluene to form carbon number eight aromatics such as para-xylene is herein disclosed. The process is based on the discovery that deactivating contaminants present in typical hydrocarbon feeds, such as chlorides, can be removed with an alumina guard bed prior to contacting with a transalkylation catalyst. Effective transalkylation catalysts have a solid-acid component such as mordenite, and a metal component such as rhenium. The invention is embodied in a process, a catalyst system, and an apparatus. The invention provides for longer catalyst cycle life when processing aromatics under commercial transalkylation conditions.

6 Claims, 1 Drawing Sheet

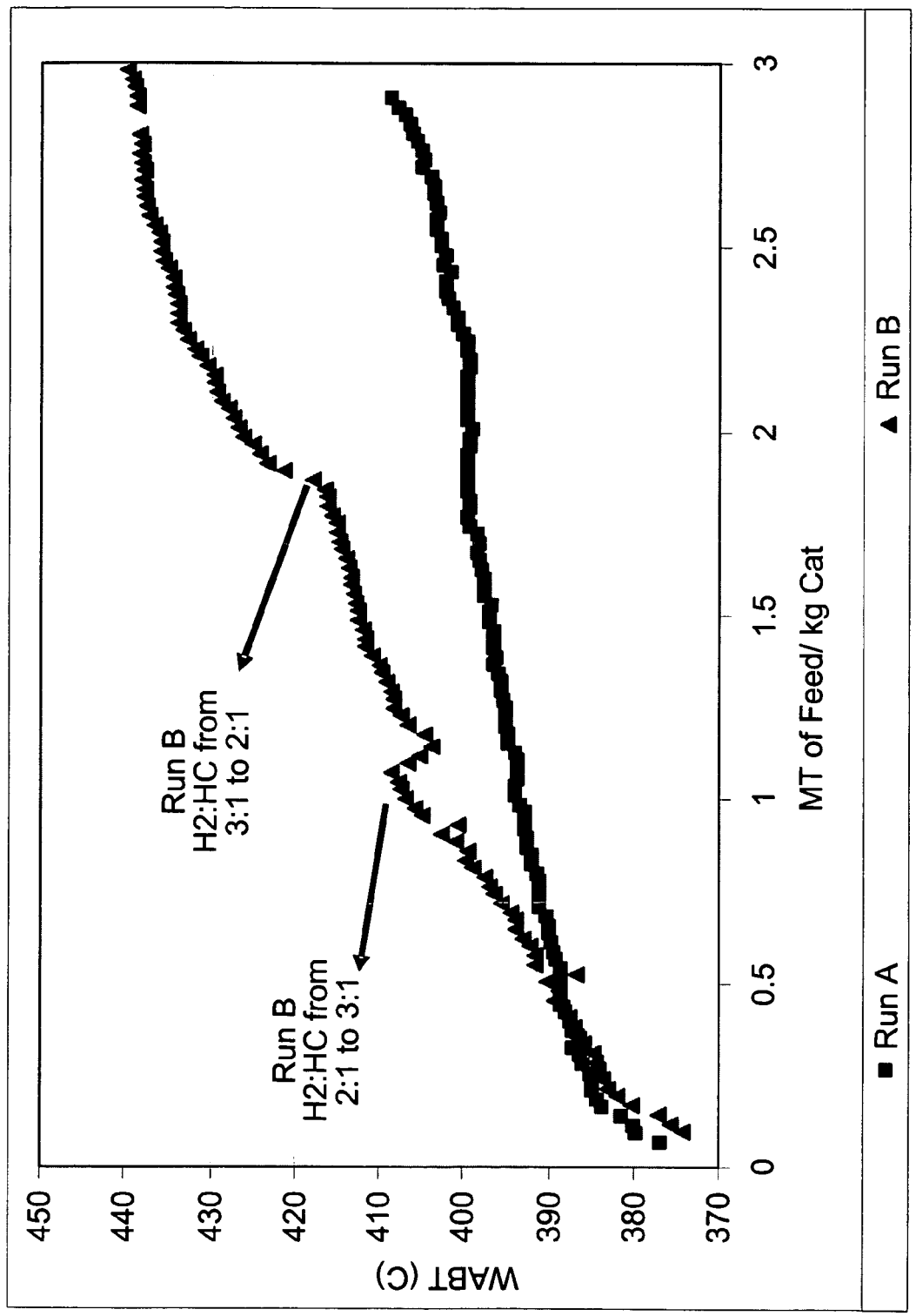

US 7,154,014 B1

ALUMINA GUARD BED FOR AROMATICS TRANSALKYLATION PROCESS

FIELD OF THE INVENTION

This invention relates to catalytic hydrocarbon conversion, and more specifically to the use of an activated alumina guard bed for extending the life of a transalkylation catalyst used in reacting aromatic $C_9^+$ compounds with toluene to produce xylenes. By decomposing contaminant species present in transalkylation feed aromatics, such as chlorides, the guard bed reduces coke formation on the transalkylation catalyst.

BACKGROUND OF THE INVENTION

Xylene isomers, para-xylene, meta-xylene and ortho-xylene, are important intermediates which find wide and varied application in chemical syntheses. Para-xylene upon oxidation yields terephthalic acid, which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene, which is difficult to separate or to convert. Para-xylene in particular is a major chemical intermediate with rapidly growing demand, but amounts to only 20 to 25% of a typical $C_8$ aromatics stream. Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Often toluene ($C_7$) is dealkylated to produce benzene ($C_6$) or selectively disproportionated to yield benzene and $C_8$ aromatics from which the individual xylene isomers are recovered.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. A higher yield of xylenes at the expense of benzene thus is a favorable objective, and processes to transalkylate $C_9$ and heavier aromatics with benzene and toluene have been commercialized to obtain high xylene yields.

U.S. Pat. No. 4,857,666 discloses a transalkylation process over mordenite and incorporating a metal modifier into the catalyst.

U.S. Pat. No. 5,763,720 discloses a transalkylation process for conversion of $C_9^+$ into mixed xylenes and $C_{10}^+$ aromatics over a catalyst containing zeolites including amorphous silica-alumina, MCM-22, ZSM-12, and zeolite beta, where the catalyst further contains a Group VIII metal such as platinum.

U.S. Pat. No. 6,060,417 discloses a transalkylation process using a catalyst based on mordenite with a particular zeolitic particle diameter and having a feed stream limited to a specific amount of ethyl containing heavy aromatics. The catalyst contains nickel or rhenium metal.

U.S. Pat. No. 6,486,372 B1 discloses a transalkylation process using a catalyst based on dealuminated mordenite with a high silica to alumina ratio that also contains at least one metal component.

U.S. Pat. No. 6,613,709 B1 discloses a catalyst for transalkylation comprising zeolite structure type NES and metals such as rhenium, indium, or tin.

U.S. Pat. No. 6,740,788 B1 discloses an integrated process for aromatics production enabled by a stabilized transalkylation catalyst having a metal function.

Many types of supports and elements have been disclosed for use as catalysts in processes to transalkylate various types of aromatics into xylenes, but there exists a problem presented by transalkylation aromatics feed stream contaminants, whereby such contaminants reduce the useful catalyst cycle life. Applicants have found a solution with the application of a contaminant removal guard bed that extends catalyst life, resulting in a more stable aromatics transalkylation process that will be more profitable over the catalyst life cycle by requiring less frequent down time for regeneration to remove deactivating coke deposits.

SUMMARY OF THE INVENTION

A principal object of the present invention is to provide a process of using a guard bed in front of a transalkylation catalyst, the guard bed catalyst system itself, and a reactor configuration for the transalkylation of alkylaromatic hydrocarbons into xylenes. More specifically, the present invention is directed to improved conversion of aromatic hydrocarbons by removal of feed contaminants. This invention is based on the discovery that feed contaminants removed in a guard bed prior to contacting the feed with a transalkylation catalyst demonstrates a process showing increased stability of xylene production under transalkylation conditions.

Accordingly, a broad embodiment of the present invention is a process for contacting an aromatics stream containing a contaminant material with a guard bed and then with a catalyst suitable for transalkylation of the aromatics into xylenes. In another embodiment, the present invention is a catalyst system combining guard bed material with catalyst material. In yet another embodiment, the present invention is a reactor configuration providing an apparatus for situating a guard bed before a catalyst bed.

These, as well as other objects and embodiments will become evident from the following detailed description of the invention.

BRIEF DESCRIPTION OF THE DRAWING

The FIGURE shows the effect of guard bed addition upon catalyst activity for transalkylation of $C_7$, $C_9$, and $C_{10}$ aromatics at a level of about 50 wt-% conversion while producing $C_8$ aromatics. The slope of the weighted average catalyst bed temperature (WABT) is proportional to stability, with a flatter slope representing greater stability.

DETAILED DESCRIPTION OF THE INVENTION

The feed stream to the present process generally comprises alkylaromatic hydrocarbons of the general formula $C_6H_{(6-n)}R_n$, where n is an integer from 0 to 6 and R is $CH_3$, $C_2H_5$, $C_3H_7$, or $C_4H_9$, in any combination. Suitable alkylaromatic hydrocarbons include, for example but without so limiting the invention, benzene, toluene, ethylbenzene, ethyltoluenes, propylbenzenes, tetramethylbenzenes, ethyldimethylbenzenes, diethylbenzenes, methylpropylbenzenes, ethylpropylbenzenes, triethylbenzenes, di-isopropylbenzenes, and mixtures thereof. The feed stream may comprise lower levels of ortho-xylene, meta-xylene, and para-xylene that are the desired products of the present process.

The feed stream also may comprise naphthalene and other $C_{10}$ and $C_{11}$ aromatics and suitably is derived from one or a variety of sources. Polycyclic aromatics such as the bi-cyclic components including naphthalene, methylnaphthalene, are permitted in the feed stream of the present invention. Indane, which is also referred to as indan or indene, is meant to define a carbon number nine aromatic species with one carbon six ring and one carbon five ring wherein two carbon atoms are shared. Naphthalene is meant to define a carbon number ten aromatic species with two carbon six rings wherein two carbon atoms are shared. Polycyclic aromatics may also be present, even in substantial amounts such as greater than about 0.5 wt-% of the feed stream.

Feed components may be produced synthetically, for example, from naphtha by catalytic reforming or by pyrolysis followed by hydrotreating to yield an aromatics-rich product. The feed stream may be derived from such product with suitable purity by extraction of aromatic hydrocarbons from a mixture of aromatic and nonaromatic hydrocarbons and fractionation of the extract. For instance, aromatics may be recovered from reformate. Reformate may be produced by any of the processes known in the art. The aromatics then may be recovered from reformate with the use of a selective solvent, such as one of the sulfolane type, in a liquid—liquid extraction zone. The recovered aromatics may then be separated into streams having the desired carbon number range by fractionation. When the severity of reforming or pyrolysis is sufficiently high, extraction may be unnecessary and fractionation may be sufficient to prepare the feed stream. Such fractionation typically includes at least one separation column to control feed end point.

The feed heavy-aromatics stream, characterized by $C_9^+$ aromatics (or $A_9^+$), permits effective transalkylation of light aromatics such as benzene and toluene with the heavier $C_9^+$ aromatics to yield additional $C_8$ aromatics that are preferably xylenes. The heavy-aromatics stream preferably comprises at least about 90 wt-% total aromatics; and may be derived from the same or different known refinery and petrochemical processes as the benzene and toluene, and/or may be recycled from the separation of the product from transalkylation. When the feed is predominantly heavy-aromatics then de-alkylation or hydrocracking of the heavy aromatics to lighter aromatics may also occur and provide additional intermediate feed components that may further convert to benzene, toluene or xylene.

Feed contaminants may be present in small amounts, such as amounts less than 100 wt-ppm, and more generally are present in amounts less than 10 wt-ppm. Feed contaminants include, but are not limited to, oxygen, chloride, sulfur, and nitrogen species.

According to the process of the present invention, the feed mixture of heavy $A_9^+$, toluene, and feed contaminants is contacted with an alumina guard bed and then with a transalkylation catalyst of the type hereinafter described in a two zone system. The first zone is the guard bed zone, while the second zone is the transalkylation zone. The guard bed may be contained in a separate vessel from the transalkylation reactor of the types hereinafter described, or it may be contained within the same reactor vessel as the transalkylation catalyst. Better flow distribution is achieved when catalyst support materials, for example inert ceramic objects, are placed in upstream and downstream positions from the alumina guard bed material. Therefore, when the two zones are placed in separate vessels appropriate piping is used to serially connect them together. When the two zones are in the same vessel, then the zones are generally layered on top or next to each other such that contacting with hydrocarbons occurs sequentially and under the same conditions. Alternatively, the zones may be intermixed, such that physical mixtures of guard bed and transalkylation particles are combined together on a bulk basis where separate particles are intermingled, or on a particulate basis where effective guard bed material is directly composited alongside catalyst material. Finally, such zones are herein described as in fluid communication with each other by being present in the same vessel, connected in series with separate vessels and piping there between for transference of the alumina guard bed product to the transalkylation reactor.

The hydrocarbon feed is passed through an alumina guard bed and produces an alumina guard bed product stream. The alumina guard bed product stream is then preferably transalkylated in the vapor phase and in the presence of hydrogen. If transalkylated in the liquid phase, then the presence of hydrogen is optional. If present, free hydrogen is associated with the feed stream and recycled hydrocarbons in an amount of from about 0.1 moles per mole of alkylaromatics up to 10 moles per mole of alkylaromatic. This ratio of hydrogen to alkylaromatic is also referred to as hydrogen to hydrocarbon ratio. The transalkylation reaction preferably yields a product having increased xylene content.

The feed to alumina guard bed zone usually first is heated by indirect heat exchange against the effluent of the transalkylation reaction zone and then is heated to reaction temperature by exchange with a warmer stream, steam or a furnace. The feed then is passed through the guard bed zone and then through a reaction zone, which may comprise one or more individual reactors. The use of a single transalkylation reaction vessel having a fixed cylindrical bed of catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons including $C_8$ aromatic compounds. This effluent is normally cooled by indirect heat exchange against the stream entering the reaction zone and then further cooled through the use of air or cooling water. The effluent may be passed into a stripping column in which substantially all $C_5$ and lighter hydrocarbons present in the effluent are concentrated into an overhead stream and removed from the process. An aromatics-rich stream is recovered as net stripper bottoms, which is referred to herein as the transalkylation effluent.

To effect a transalkylation reaction, the present invention incorporates a transalkylation catalyst in at least one zone, but no limitation is intended in regard to a specific catalyst other than such catalyst must possess a solid-acid component and a metal component. Conditions employed in the transalkylation zone normally include a temperature of from about 200° to about 540° C. The transalkylation zone is operated at moderately elevated pressures broadly ranging from about 100 kPa to about 6 MPa absolute. The transalkylation reaction can be effected over a wide range of space velocities. Weight hourly space velocity (WHSV) generally is in the range of from about 0.1 to about 20 $hr^{-1}$. Such transalkylation conditions are similar to the alumina guard bed conditions.

The transalkylation effluent is separated into a light recycle stream, a mixed $C_8$ aromatics product and a heavy recycle stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone or the alumina guard bed zone. The heavy recycle stream contains substantially all of the $C_9$ and heavier aromatics and may be partially or totally recycled to the transalkylation reaction zone or the alumina guard bed zone as well.

Several types of alumina guard bed materials may be used in the present invention including gamma alumina, theta alumina, and other alumina phase materials having high surface areas generally greater than about 25 $m^2/g$, with gamma phase alumina being preferred. Alpha phase alumina generally has a low surface area is not generally suitable for the present invention. Gamma phase alumina is obtained by aging and calcining aluminum trihydroxides [$Al(OH)_3$], aluminum oxyhydroxides [AlOOH], transition aluminas derived from $Al(OH)_3$ and AlOOH, and, optionally metal promoters with any combination thereof. Generally, alumina will be precipitated from an aqueous solution containing Al+3 ions. Such precipitate is aged, filtered, washed and dried. During these operations alumina passes through various phases. Typically, the initial precipitation leads to a gel with minute crystals of boehmite. The gel can be aged at a temperature of about 80° C. into crystalline boehmite that forms gamma-phase alumina upon a calcination temperature of about 600° C. Gamma phase alumina has a high surface area, generally between 100 and 300 $m^2/g$. Upon heating to higher temperatures of about 1100° C. or more, the alumina moves through theta or delta phases to becomes alpha phase and has a low surface area less than 25 $m^2/g$ and commonly less than 1 $m^2/g$.

Several types of transalkylation catalysts that may be used in the present invention are based on a solid-acid material combined with an optional metal component. Suitable solid-acid materials include all forms and types of mordenite, mazzite (omega zeolite), beta zeolite, ZSM-11, ZSM-12, ZSM-22, ZSM-23, MFI type zeolite, NES type zeolite, EU-1, MAPO-36, MAPSO-31, SAPO-5, SAPO-11, SAPO-41, and silica-alumina or ion exchanged versions of such solid-acids. For example, in U.S. Pat. No. 3,849,340 a catalytic composite is described comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of less than 30:1 and a metal component selected from copper, silver and zirconium. Refractory inorganic oxides, combined with the above-mentioned and other known catalytic materials, have been found useful in transalkylation operations. For instance, silica-alumina is described in U.S. Pat. No. 5,763,720. Crystalline aluminosilicates have also been employed in the art as transalkylation catalysts. ZSM-12 is more particularly described in U.S. Pat. No. 3,832,449. Zeolite beta is more particularly described in Re. 28,341 (of original U.S. Pat. No. 3,308,069). A favored form of zeolite beta is described in U.S. Pat. No. 5,723,710, which is incorporated herein by reference. The preparation of MFI topology zeolite is also well known in the art. In one method, the zeolite is prepared by crystallizing a mixture containing an alumina source, a silica source, an alkali metal source, water and an alkyl ammonium compound or its precursor. Further descriptions are in U.S. Pat. No. 4,159,282, U.S. Pat. No. 4,163,018, and U.S. Pat. No. 4,278,565. The synthesis of the Zeolite Omega is described in U.S. Pat. No. 4,241,036. ZSM intermediate pore size zeolites useful in this invention include ZSM-5 (U.S. Pat. No. 3,702,886); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842). European Patent EP 0378916 B1 describes NES type zeolite and a method for preparing NU-87. The EUO structural-type EU-1 zeolite is described in U.S. Pat. No. 4,537,754. MAPO-36 is described in U.S. Pat. No. 4,567,029. MAPSO-31 is described in U.S. Pat. No. 5,296,208 and typical SAPO compositions are described in U.S. Pat. No. 4,440,871 including SAPO-5, SAPO-11 and SAPO-41. Typically, the solid-acid component will be present in the catalyst in an amount from about 1 to about 99 wt-%.

A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder. Typically the binder may be present in about 5 to about 95 wt-% of the catalyst when it is used.

The catalyst also may contain a metal component. One preferred metal component is a Group VIII (IUPAC8-10) metal that includes nickel, iron, cobalt, and platinum-group metal. Of the platinum group, i.e., platinum, palladium, rhodium, ruthenium, osmium and iridium, platinum is especially preferred. Another preferred metal component is rhenium and it will be used for the general description that follows. This metal component may exist within the final catalytic composite as a compound such as an oxide, sulfide, halide, or oxyhalide, in chemical combination with one or more of the other ingredients of the composite. The rhenium metal component may be incorporated in the catalyst in any suitable manner, such as coprecipitation, ion-exchange, co-mulling or impregnation. The preferred method of preparing the catalyst involves the utilization of a soluble, decomposable compound of rhenium metal to impregnate the carrier material in a relatively uniform manner. Typical rhenium compounds which may be employed include ammonium perrhenate, sodium perrhenate, potassium perrhenate, potassium rhenium oxychloride, potassium hexachlororhenate (IV), rhenium chloride, rhenium heptoxide, perrhenic acid, and the like compounds. Preferably, the compound is ammonium perrhenate or perrhenic acid because no extra steps may be needed to remove any co-contaminant species. This component may be present in the final catalyst composite in any amount which is catalytically effective, generally comprising about 0.01 to about 2 wt-% of the final catalyst calculated on an elemental basis.

The catalyst may optionally contain additional metal components along with those metal components discussed above or include additional metal components instead of those metal components in their entirety. Additional metal components of the catalyst include, for example, tin, germanium, lead, and indium and mixtures thereof. Catalytically effective amounts of such additional metal components may be incorporated into the catalyst by any means known in the art. A preferred amount is a range of about 0.01 to about 2.0 wt-% on an elemental basis.

One shape of the catalyst of the present invention is a cylinder. Such cylinders can be formed using extrusion methods known to the art. Another shape of the catalyst is one having a trilobal or three-leaf clover type of cross section that can be formed by extrusion. Another shape is a sphere that can be formed using oil-dropping methods or other forming methods known to the art.

At least one oxidation step may be used in the preparation of the catalyst. The conditions employed to effect the oxidation step are selected to convert substantially all of the metallic components within the catalytic composite to their corresponding oxide form. The oxidation step typically takes place at a temperature of from about 370° to about 650° C. An oxygen atmosphere is employed typically comprising air. Generally, the oxidation step will be carried out for a period of from about 0.5 to about 10 hours or more, the exact period of time being that which is required to convert substantially all of the metallic components to their corresponding oxide form. This time will, of course, vary with the oxidation temperature employed and the oxygen content of the atmosphere employed.

In preparing the catalyst, a reduction step may be employed. The reduction step is designed to reduce substantially all of the metal components to the corresponding elemental metallic state and to ensure a relatively uniform and finely divided dispersion of this component throughout the catalyst.

Finally, the catalytic composite is subjected to an optional sulfur treatment or pre-sulfiding step. The sulfur component may be incorporated into the catalyst by any known technique. Any one or a combination of in situ and/or ex situ sulfur treatment methods is preferred. The resulting catalyst mole ratio of sulfur to rhenium is preferably from about 0.1 to less than about 1.5.

EXAMPLES

The following examples are presented only to illustrate certain specific embodiments of the invention, and should not be construed to limit the scope of the invention as set forth in the claims. There are many possible other variations, as those of ordinary skill in the art will recognize, within the scope of the invention.

Example 1

A transalkylation catalyst comprising mordenite was prepared for comparative pilot-plant testing by the forming process called extrusion. Typically, 2500 g of a powder blend of 25 wt-% alumina (commercially available under the trade names CATAPAL B and/or VERSAL 250) and 75 wt-% mordenite (commercially available under the trade name ZEOLYST CBV-21A) was added to a mixer. A solution was prepared using 10 g nitric acid (67.5 wt-% $HNO_3$) with 220 g deionized water and the solution was stirred. The solution was added to the powder blend in the mixer, and mulled to make dough suitable for extrusion. The dough was extruded through a die plate to form cylindrically shaped (0.08 cm diameter) extrudate particles. The extrudate particles were calcined at about 565° C. with 15 wt-% steam for 2 hours.

The catalyst was finished using the extrudate particles and an evaporative impregnation with rhenium metal by using an aqueous solution of ammonium perrhenate ($NH_4ReO_4$). The impregnated base was calcined in air at 540° C. for 2 hours and resulted in a metal level of 0.15 wt-% rhenium. Next the catalyst was reduced for 12 hours in substantially dry hydrogen at 500° C.

Example 2

The catalyst was tested for aromatics transalkylation ability in a pilot plant using an aromatics feed blend of $C_7$, $C_9$, and $C_{10}$ aromatics to demonstrate effectiveness of using an alumina guard bed to remove contaminant chlorides when producing $C_8$ aromatics. The feed properties are listed in the table below.

| Feed | Wt-% |
|---|---|
| Non Aromatics | 0.11 |
| Benzene | 0.00 |
| Toluene | 44.33 |
| Ethylbenzene | 0.01 |
| Mixed Xylenes | 0.37 |
| Propylbenzene | 3.98 |
| Ethyltoluene | 20.64 |
| Trimethylbenzene | 17.90 |
| DEB + C10A | 3.74 |
| Ethyl Xylenes | 5.21 |
| Tetramethylbenzene | 1.41 |
| Butylbenzene | 0.40 |
| Indane | 1.22 |
| C11+ | 0.67 |
| Total | 100.0 |

Methylene chloride was also present in the feed at an amount of 3.0 wt-ppm.

The test consisted of loading a vertical down-flow reactor with 60 cc catalyst located below 240 cc alumina particles. Two types of alumina particles were loaded in two different tests. First, a gamma-phase alumina oxide (obtained by calcining crystalline boehmite at approximately 600° C.) having 185 $m^2$/g surface area was loaded in Run A. Second, commercially available corundum, alpha-phase aluminum oxide with 0.83 $m^2$/g surface area was loaded in Run B.

The loaded reactors were contacted with the feed at 2860 kPa abs (400 psig) under a space velocity (WHSV) of 4 $hr^{-1}$ and hydrogen to hydrocarbon ratio ($H_2$/HC) of 2. A conversion level of about 50 wt-% of feed aromatics was achieved during the initial part of testing. The FIGURE shows the effect of guard bed addition upon catalyst activity for transalkylation of $C_7$, $C_9$, and $C_{10}$ aromatics at a level of about 50 wt-% conversion while producing $C_8$ aromatics. The slope of the weighted average catalyst bed temperature (WABT) is related to stability where the flatter slope represents more stable operation and where higher slope represents less stability and increased catalyst deactivation. Run B, with the alpha alumina guard bed, also indicates a time period wherein the hydrogen to hydrocarbon ratio was increased from 2:1 to 3:1, without approaching the stability of Run A, with the gamma alumina guard bed.

The data showed that the addition of a high surface area gamma phase alumina guard bed improved the stability over a comparable low surface area alumina phase guard bed. Even under conditions of increased hydrogen to hydrocarbon ratio, the stability difference persisted. After testing, the alumina and catalyst chloride contents were analyzed for each run. Alpha alumina showed about 0.01 wt-% chloride in front of a catalyst that showed about 0.25 wt-% chloride. In contrast, gamma alumina showed approximately 1.2 wt-% chloride in front of a catalyst that showed about 0.01 wt-% chloride. Accordingly, the gamma alumina guard bed permitted extended operation of an effective transalkylation catalyst by removing contaminant feed species.

What is claimed is:

1. A process for converting a hydrocarbon feed comprising $C_9^+$ aromatic compounds or a toluene compound, and at least one contaminant species compound, said process comprising:

(a) a first step of contacting the feed with a high surface area alumina guard bed comprising an activated alumina component having gamma phase under guard bed conditions including a temperature from about 200° to about 540° C. to produce a guard bed product; and (b) a second step of contacting the guard bed product with a transalkylation catalyst comprising a solid-acid component selected from the group consisting of mordenite, mazzite, zeolite beta, ZSM-11, ZSM-12, ZSM-22, ZSM-23, MFI topology zeolite, NES topology zeolite, EU-1, MAPO-36, MAPSO-31, SAPO-5, SAPO-11, SAPO-41, silica-alumina and mixtures thereof under transalkylation conditions to produce a transalkylation product containing $C_8$ aromatic compounds.

2. The process of claim 1 wherein the alumina guard bed comprises an activated alumina with a surface area of greater than about 25 $m^2/g$.

3. The process of claim 1 wherein the guard bed conditions comprise a pressure from about 100 kPa to about 6 MPa absolute and a space velocity from about 0.1 to about 20 $hr^{-1}$.

4. The process of claim 1 wherein the transalkylation conditions comprise a temperature from about 200° to about 540° C., a pressure from about 100 kPa to about 6 MPa absolute, and a space velocity from about 0.1 to about 20 $hr^{-1}$.

5. The process of claim 1 wherein the contaminant species compound is selected from the group consisting of oxygen, chloride, sulfur, nitrogen and mixtures thereof.

6. The process of claim 1 wherein the transalkylation catalyst further comprises a metal component selected from the group of platinum-group Metal, tin, lead, indium, germanium, rhenium, nickel, iron, cobalt or a combination thereof thereof.

* * * * *